United States Patent [19]

Takakura et al.

[11] Patent Number: 4,775,628

[45] Date of Patent: Oct. 4, 1988

[54] PETRI DISH FOR CULTIVATING BACTERIA AND METHOD OF INSPECTING DRUG SUSCEPTIBILITY

[75] Inventors: Tetsuya Takakura, Osaka; Kenzi Asano, Hyogo; Kazuyuki Sugahara, Nagasaki, all of Japan

[73] Assignee: Kobayashi Pharmaceutical Co., Ltd., Osaka, Japan

[21] Appl. No.: 774,757

[22] Filed: Sep. 11, 1985

[30] Foreign Application Priority Data

Oct. 9, 1984 [JP] Japan .................. 59-212163

[51] Int. Cl.⁴ .................................. C12M 1/22
[52] U.S. Cl. .................... 435/298; 435/297; 435/301
[58] Field of Search ............ 435/297, 298, 299, 300, 435/301

[56] References Cited

U.S. PATENT DOCUMENTS

| | | | |
|---|---|---|---|
| 2,954,327 | 9/1960 | Kanz | 435/299 |
| 3,055,808 | 9/1962 | Henderson | 435/298 |
| 3,630,849 | 12/1971 | Land et al. | 435/297 X |
| 3,729,382 | 4/1973 | Shaffer et al. | 435/297 X |
| 3,809,617 | 5/1974 | Schmitt | 435/299 |
| 4,271,270 | 6/1981 | Lukacsek | 435/297 X |
| 4,435,508 | 3/1984 | Gabridge | 435/299 X |
| 4,476,226 | 10/1984 | Hansen et al. | 435/299 |

FOREIGN PATENT DOCUMENTS

3102571 9/1982 Fed. Rep. of Germany ...... 435/297

Primary Examiner—John Rivell
Attorney, Agent, or Firm—Koda & Androlia

[57] ABSTRACT

A Petri dish for cultivating bacteria used for isolating the bacteria in an enrichment culture for performing drug susceptibility tests, etc. having a mouth covered with at least one sheet and at least one small opening provided on the bottom of the Petri dish, partitions having a height equal to the distance between the bottom of the Petri dish and the sheet may be provided in the Petri dish, and a sealing lid may be fitted over the small openings. A method of inspecting drug susceptibility of bacteria which are isolated from clinical specimens etc. or purely cultured after their isolation using the Petri dish. The method using the fractionized Petri dish having a pervious sheet as the cultivation surface assorts different kinds of media from each other, the media being different in the kind of drug contained in each media or media containing the same drug but in different concentrations in each section of the Petri dish into which the bacteria is inoculated.

4 Claims, 10 Drawing Sheets

PETRI DISH FOR CULTIVATING BACTERIA AND METHOD OF INSPECTING DRUG SUSCEPTIBILITY

BACKGROUND OF THE INVENTION

1. Field of the Invention

The present invention relates to a Petri dish for cultivating bacteria which is used for isolating bacteria, an enrichment culture, drug susceptibility tests, etc. and a method of inspecting drug susceptibility of bacteria which are isolated from a clinical specimen etc. or purely cultured after isolation by using the Petri dish.

2. Prior Art

When performing bacterial inspection in a hospital, in order to detect the pathogen to which the infectious disease is ascribed, it is necessary to perform operations such as isolation of the culture and enrichment of the bacterial culture from the material to be inspected. Particularly, the results obtained from bacterial inspection are very important since recent trends make it more difficult to identify pathogenic bacteria through clinical diagnosis due to complicated pathologic configurations of infectious diseases.

However, media suitable for growth of bacteria varies depending upon the kind of bacteria. Thus, when screening pathogenic bacteria, an adequate medium must be prepared for the growth of each detectable pathogenic bacteria possibly present. Bacteria which can be found in blood specimens are: staphylococcus, streptococcus, pneumococcus, enterococcus, haemophylus, salmonella, *escherichia coli, pseudomonas aerouginosa, anaerobic bacterium,* campylobacter, brucella, etc. In order to isolate any of these bacteria, it is usually necesary to prepare media including blood agar medium chocolate agar medium, isolation medium for anaerobic bacterium, medium for enrichment, etc. for every specimen.

Furthermore, salmonella, *dysentery bacillus, pathogenic coli, yersinia enterocolitica, klebsiella oxytoca,* vibrio, staphylococcus, *bacillus cereus,* etc. can be detected from feces and the media needed for any of these bacteria include preparations of BTB lactose agar medium, DHL agar medium, SS agar medium, isolation medium for anaerobic bacterium, medium for enrichment, etc.

When producing these media with a conventional Petri dish for cultivating bacteria, it is necessary to heat the media solution for a long time because the media contains agar. Also, the Petri dish must be placed in a horizontal, stationary position in order to facilitate coagulation of the agar. In addition, almost all conventional Petri dishes for cultivating bacteria have one medium prepared per set of Petri dishes. Thus, the number of Petri dishes required for one specimen is increased and inoculations must be performed one at a time for each one.

With the above-disadvantages in mind, a method was conceived wherein several kinds of media are poured separately into a fractionalized (or sectioned) Petri dish. However, the inside of the dish must be provided with partitions since the inoculation procedure must be performed section by section (fraction by fraction). Because the prepared media is different in levels from one section to another, there is no improvement in using a sectioned or fractionalized Petri dish since individual mediums must be prepared for each section and further, since each section must be individually inoculated as in the above-described method using one Petri dish per medium.

Furthermore, in order to prepare various kinds of plate media using a conventional Petri dish for cultivating bacteria, in addition to the necessary complicated steps of preparing the solution, sterilization, separate pouring and coagulation of the components of the media; each operation must be performed in an aseptic atmosphere as possible. Usually, separate pouring of one medium per Petri dish increases the number of Petri dishes necessary for one specimen. Therefore, it is almost impossible to adequately prepare the necessary amount of media required in a hospital's test room where the number of specimens and the kind of bacteria handled are not always constant. For this reason, many facilities make or purchase the estimated amount of media necessary for a predetermined period at one time and use it gradually, storing it in a refrigerator. In this case, since the media when purchased and/or stored is only protected by a fitted lid around the top of the container containing the media, there is a problem in that humidity and/or various bacteria may contaminate the media.

When conventional media is used it must be dried in advance, but media which is in the de-airing state during storage or at the time of purchase has oxygen dissolved in the air during such drying process so that, if anaerobic bacteria are handled, it is necessary to leave the media in an anaerobic chamber after drying.

Also, when applying chemotherapy to bacterial infectious diseases, selecting and using a drug which is most effective in causing the bacterium such as the disease is recommended. Nevertheless, the kind and concentration of the drug which will be effective on the bacteria varies depending on the kind of bacteria, and the recent spread of chemotherapy triggers the appearance of bacterial stock (resistant bacteria) which shows a tolerance to a druge which has been conventionally effective. Therefore, if it is determined that a particular bacterium is causing an infectious disease, it is almost impossible to assume an effective drug. Due to the above, for the purpose of putting therapy which is clinically adequate and reasonable into practice, it should not be forgotten that drug susceptibility inspection is one of the most important procedures when inspecting bacterium.

Methods of inspecting the drug susceptibility of bacteria include the dilution method, the diffusion method, and nephelometry. The agar plate dilution method used an agar medium and the broth dilution method belongs to the dilution method. The sensitive tablet method, the sensitivity disk method, the decantation plate method, and the vertical diffusion method are diffusion methods. In terms of the actual site where the bacteria is inspected, however, the agar plate dilution method and sensitivity disk method are used mainly from an operation-oriented perspective.

The sensitivity disk method is used to make a judgment based upon a biogenetic inhibition circle or inhibition zone of the bacteria to be tested which occurs in response to diffusion of the drug after cultivating the bacteria in the media, the bacteria to be tested is inoculated in advance, when the bacteria does not contain the drug and then a paper disk impregnated with the drug is subsequently placed thereon for a predetermined time. Although this method is widely utilized because it is easily performed and permits testing a plurality of drugs and concentration samples with one Petri dish, it causes thickness, inclination, or the kind of medium on which the disk is placed causes the inhibition circle to flucuate in magnitude so it is likely to lack reproducibility. On the other hand, method using a three-concentration disc, wherein a judgment is made on the basis of only the existence of an inhibition circle, not its magnitude, is sometimes used. However, since the setup width of the drug concentration is larger, such a method is not suitable for measuring the minimum inhibitory concentration (MIC) of the bacteria to be tested.

The agar plate dilution method uses media having a predetermined concentration of the drug contained therein in advance. This is better for reproducibility and can freely set the concentration of the drug. However, since one medium per drug or concentration setup must be used and inoculation must be performed for every media, making this method is complicated.

The purpose of conventional drug susceptibility inspection is to obtain a treating principle regarding the drug concentration at which growth of all of the bacteria is inhibited. However, it disregards the degree of drug susceptibility of the stock of bacteria to be tested corresponding to each drug concentration. In order to obtain more adequate principles as to the infectious disease, which has a tendency to be complicated, it is necessary to collect further detailed information on the bacteria causing such disease.

SUMMARY OF THE INVENTION

The object of the present invention is solve the problems in conventional Petri dishes for cultivating bacteria. Specifically, the present invention will solve not only the complicated procedures required to prepare the media but also the extremely inefficient inoculation method wherein bacteria is inoculated into one medium one at a time.

It is further an object of the present invention to solve the problem of the media getting dried or contaminated by humidity and various bacteria during storage and/or while in transit.

It is still a further object of the present invention to solve the problems such as the complicates procedures required to prepare the media and inoculation of the above-mentioned conventional inspecting method and lower reproducibility of the sensitivity disk method.

In order to accomplish the above object, in the present invention the mouth of the upper end of the Petri dish is covered with at least one sheet, the bottom of the Petri dish is provided with at least one aperture, and, if necessary, partitions of an height equal to the distance between the bottom of the Petri dish and the above-mentioned sheet, and a sealing lid mounted on the foregoing small aperture.

The sheet may be pervious to the component of the media (hereinafter referred to as the pervious sheet) with which the Petri dish is filled and may be adapted to be able to hold bacteria. It is also possible to adapt the sheet to be a sheet impervious to the component media (hereinafter referred to as the impervious sheet), in which case the sheet needs to be able to detachably cover the Petri dish proper. The impervious sheet can be adapted to be impervious also to water and oxygen. It is further acceptable to detachably cover the outside of the pervious sheet with the impervious sheet.

The method of the present invention, using the fractionized Petri dish with the pervious sheet as the cultivation surface combines different types of media. The media may vary in the type of drug contained in each medium or may contain the same type of drug but in different concentrations in each fraction (section), into which the bacteria is inoculated, thereby solving the problems of the above-mentioned conventional method.

Thus, preparation of media can be easily and aseptically performed by pouring separately the packing for the medium into the Petri dish from the small aperture provided on the bottom of the Petri dish and, when performing inoculation operation, unification of the height of the cultivation surface by the sheet enables the entire region of the fractionized medium to be inoculated with bacteria in one step.

When using an impervious sheet, the medium does not get dried, or humidity and various bacteria do not contaminate the medium during storage or transit. Since the medium is sealed so as to not directly contact air, deterioration due to oxidation is inhibited. Also at the time of the inoculation operation, when the impervious sheet is removed, a cultivation surface of the same plane can be obtained, even if them medium is fractionized, thereby inoculating the bacteria into the entire fractionized medium in one step.

DETAILED DESCRIPTION OF THE INVENTION

A description of the embodiment according to the present invention will be made in conjunction with the accompanying drawing.

FIGS. 1 to 6 illustrate the embodiment using the perivous sheet.

Figure 1:
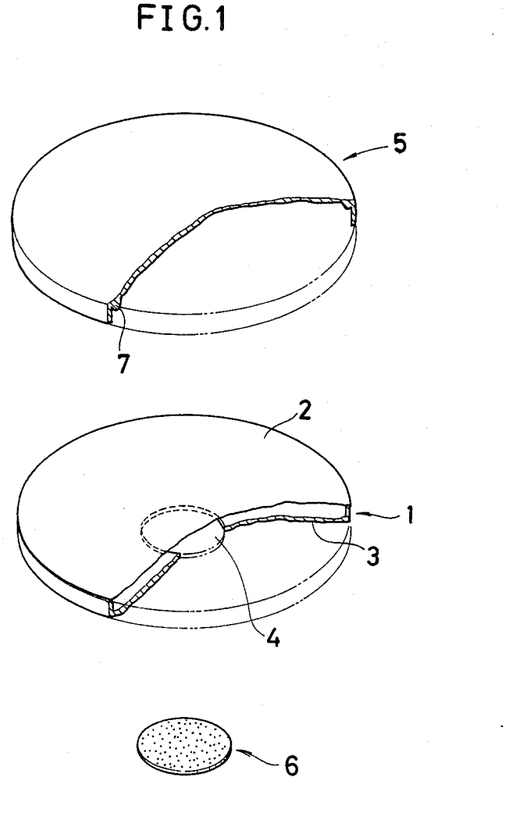
FIG. 1 is a partially cut-away exploded perspective view of the first embodiment of the Petri dish for cultivating bacteria of the present invention using a pervius sheet.

Numeral 1 is a Petri dish which is made of materials such as plastic or glass and is preferably transparent. The mouth in the upper edge of the Petri dish is covered with a pervious sheet 2, and the bottom 3 of the Petri dish is provided with a small aperture 4.

The above mentioned pervious sheet 2 needs to be provided with fine holes or clearances so that the components of the medium filled between the Petri dish 1 and the pervious sheet 2 can be leached out to the surface of the pervious sheet 2. As to the material of the pervious sheet, a porous film or a porous rubber film or membrane comprising synthetic resins such as cellulose ester sytem, polypropylene system, polycarbonate system, polyvinylidene fluoride, polymer belonging to aromatic system, etc. may be preferably used. When the medium filling the Petri dish contains a solidifying agent such as agar, etc. materials such as cloth, paper, etc., the clearance of which being wider, may be applicable. If a synthetic resin film which is hydrophobic is used, an advance hydrophilic treatment must be applied thereto.

As for the strength of the pervious sheet 2, the only requirement is that it must lie flat when the Petri dish is filled with medium. If the material needs any reinforcement, synthetic fiber, etc. can be used. Also, in the case of solid medium, reinforcement can be achieved by inserting a flat reinforcing member into the space between the pervious sheet 2 and the Petri dish lid 5, which will be explained later, until the medium is solidified.

Furthermore, the small aperture 4 on the bottom 3 of the Petri dish 1 preferably needs to be provided with a sealing lid 6 in a detachable manner when the medium in the Petri dish contains a solidifying agent such as agar so that the inside of the Petri dish 1 which has been sterilized can be kept aseptic. However, such sealing lid is not necessarily required.

Figure 2:
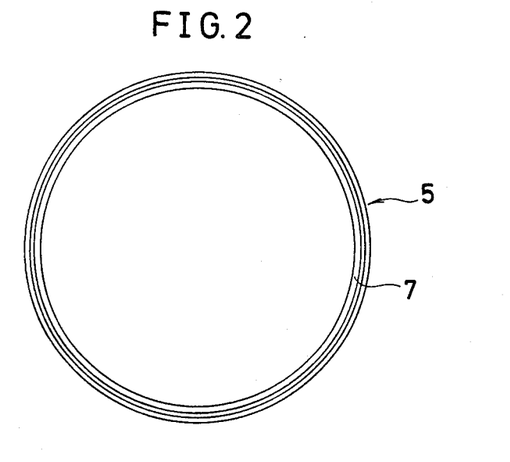
FIG. 2 is a bottom view of the lid of the Petri dish of the first embodiment.
Figure 3:
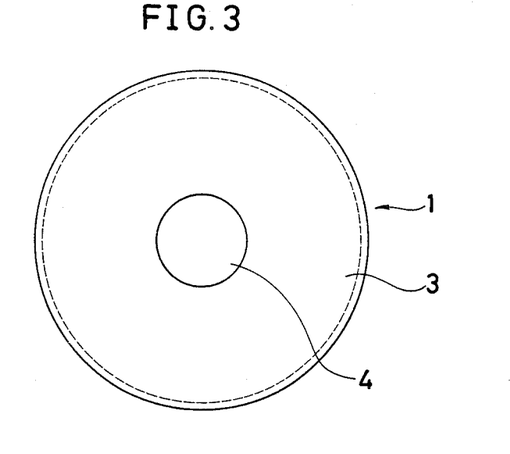
FIG. 3 is a bottom view of the Petri dish of the first embodiment.

Numeral 5 is a Petri dish lid which is made of plastic or glass and is preferably transparent. The internal periphery of the lid 5 is formed with an annular projection 7. This projection 7 forms a gap between the pervious sheet 2 and the Petri dish 5. When the Petri dish lid 5 is fitted onto the Petri dish 1. Thus, a colony of bacteria grown on the surface of the pervious sheet 2 is prevented from sticking to the internal surface of the Petri dish lid 5 and can be kept adequately air-tight. Incidently, while the projection 7 is provided on the internal periphery of the Petri dish lid 5, it is not limited to this place and it is possible to form the projection 7 on the periphery of the pervious sheet 2 or on the periphery on the upper edge of the Petri dish 1.

Figure 4:
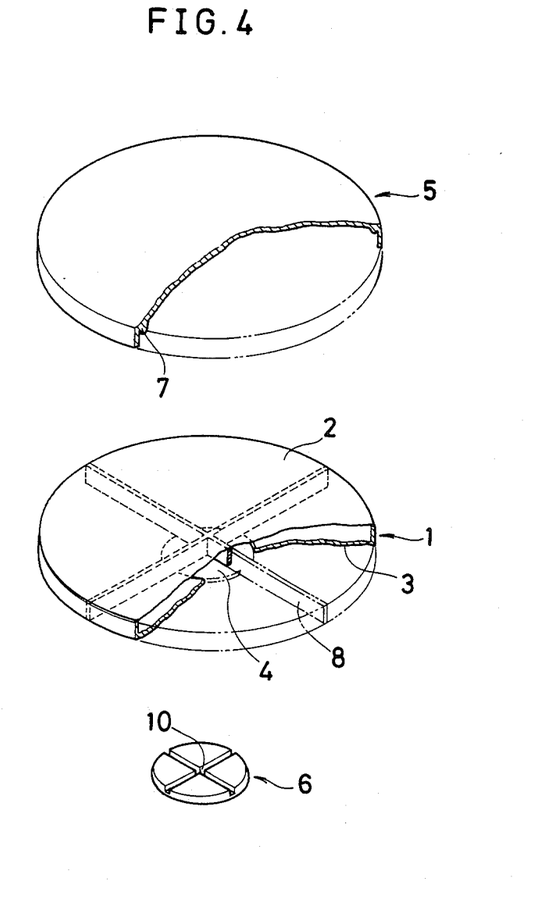
FIG. 4 is a partially cut-away exploded perspective view of the second embodiment of the present invention.
Figure 5:
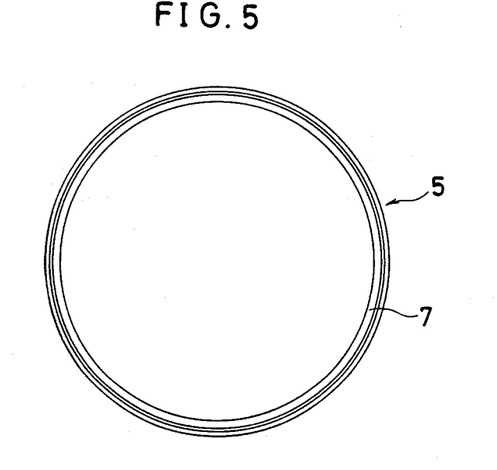
FIG. 5 is a bottom view of the lid of the Petri dish of the second embodiment.
Figure 6:
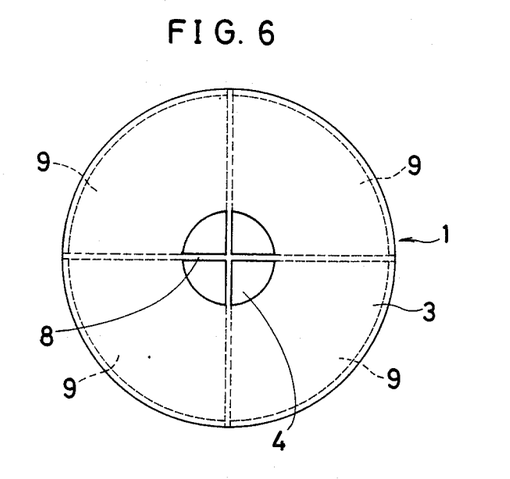
FIG. 6 is a bottom view of the Petri dish of the second embodiment.

The above-mentioned Petri dish 1 can be provided with partitions 8 on the bottom. The top of the partitions reach the pervious sheet 2 which cover the Petri dish 1. In this case, all the sections 9 formed by the paritions 8 must be provided with small aperture 4, respectively. As shown in FIGS. 4 to 6, for example, when four partitions are provided, small apertures 4 at the center of the bottom 3 of the Petri dish 1 can communicate with each of the sections 9. In this case, the sealing lid 6 can be used as a plug having a cross slit 10 as shown in FIG. 4.

FIGS. 7 to 11 illustrate an embodiment using an impervious sheet. The Petri dish 1 is detachably covered with an impervious sheet 11. The impervious sheet 11 can be of any thickness but must be impervious to water and oxygen. The material used to make up the impervious sheet is preferably a synthetic resin membrane or film which is higher in oxygen gas barrier properties, such as polyacrylonitrile nylon, polymethacrylonitrile, ethylene vinyl alcohol polymer, polyvinylidene chloride, polyethylene terephthalate, polyvinyl chloride, etc. Other materials on which the above listed resins which have higher oxygen gas barrier properties or metallic foil such as aluminum foil, etc. is laminated can meet the requirements of the present invention as long as they fulfull the relevant purpose. The thickness of the impervious sheet 11 is subject to the material it is composed of, but meets the requirements only if the strength of the material allows the surface of the medium to remain flat when the Petri dish is being filled with the medium.

Figure 7:
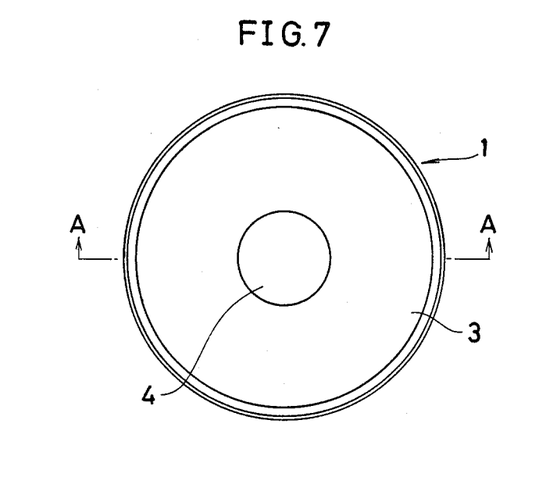
FIG. 7 is a bottom view of the third embodiment of the present invention using an impervious sheet.
Figure 8:
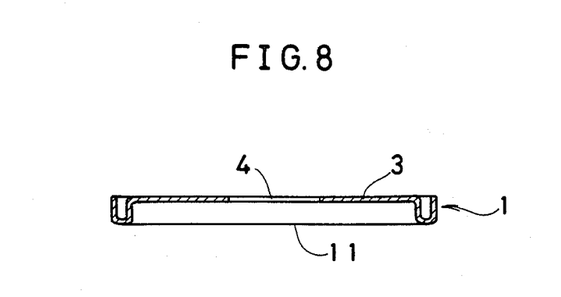
FIG. 8 is a sectional view taken on the line A—A of FIG. 7.

In the case of a solid medium, a flat reinforcing member is inserted into the gap between the impervious sheet 11 and the Petri dish lid 5 until the medium is solidified to ensure reinforcement thereof. Furthermore, if the small aperture 4 on the bottom 3 of the Petri dish is covered detachably with a sealing lid 6, it is preferable for the inside of the Petri dish, which as already been sterilized, to become aseptic. If so, when media is poured separately into the Petri dish, similar to a conventional Petri dish, a completely aseptic Petri dish can be provided.

Figure 9:
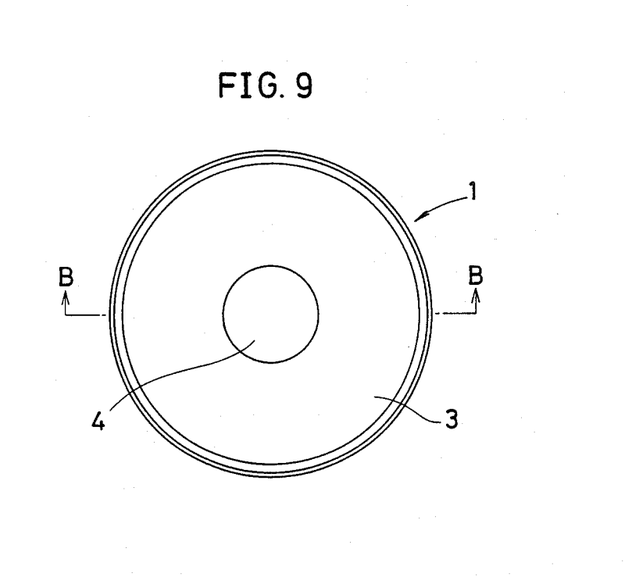
FIG. 9 is a bottom view of the Petri dish of the fourth embodiment.
Figure 10:
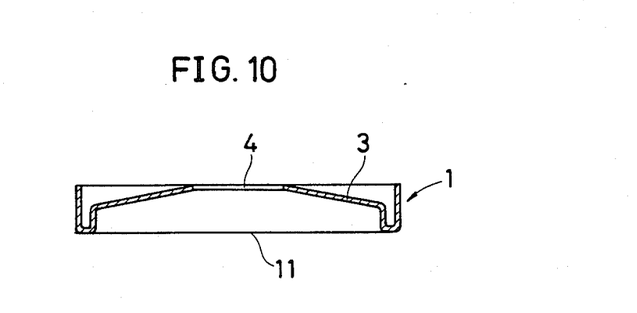
FIG. 10 is a sectional view taken on the line B—B of FIG. 9.

As shown in the embodiment of FIGS. 9 and 10, the bottom 3 of the Petri dish 1 can be provided with an inclination from the periphery of the Petri dish 1 to the small aperture 4. In this case, when pouring the media separately into the Petri dish, it is possible to fill the Petri dish with media without any foam occurring.

Figure 11:
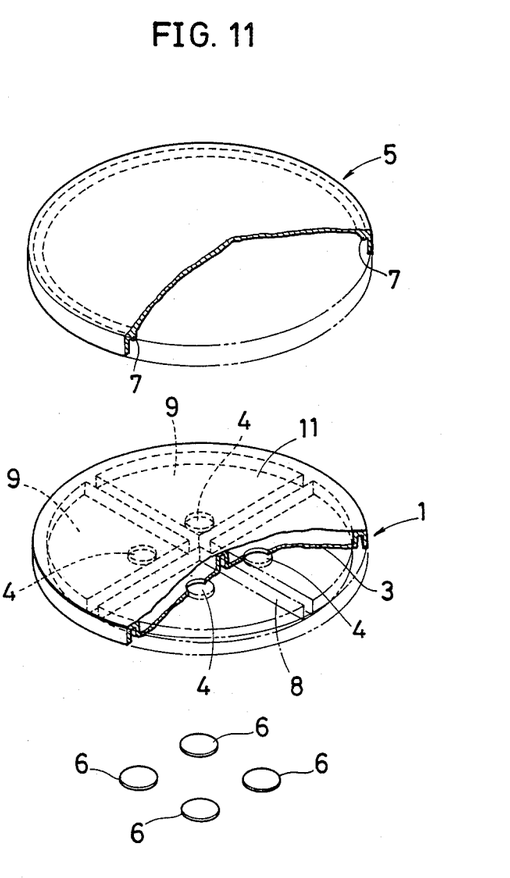
FIG. 11 is a partially cut-away exploded perspective view of the fifth embodiment of the present invention.
Figure 12:
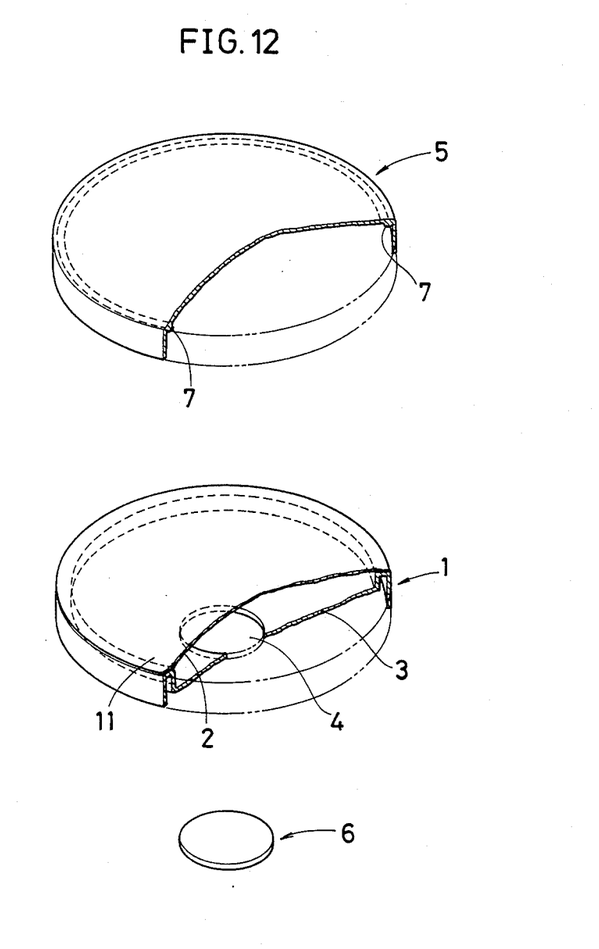
FIG. 12 is a partially cut-away exploded perspective view of the sixth embodiment of the present invention illustrating an Petri dish using both a pervious and impervious sheet.
Figure 13:
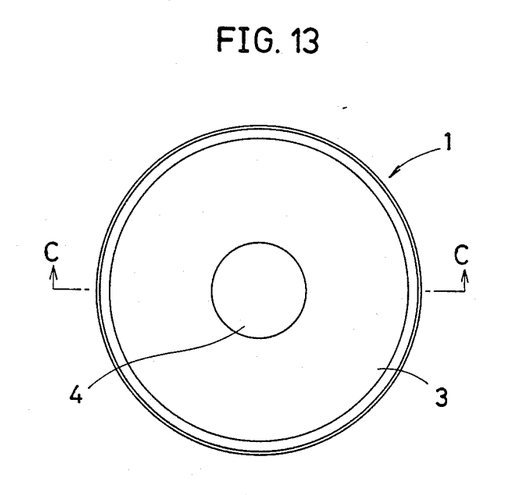
FIG. 13 is a bottom view of the Petri dish of the sixth embodiment of the present invention.
Figure 14:
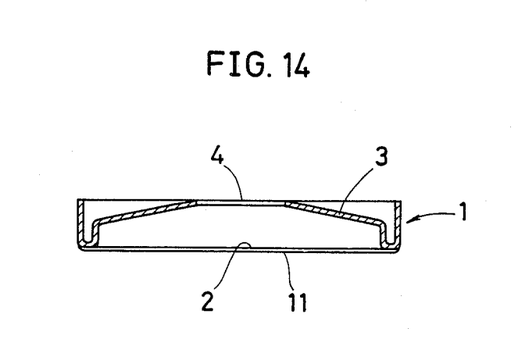
FIG. 14 is a sectional view taken on the line C—C of FIG. 13.
Figure 15:
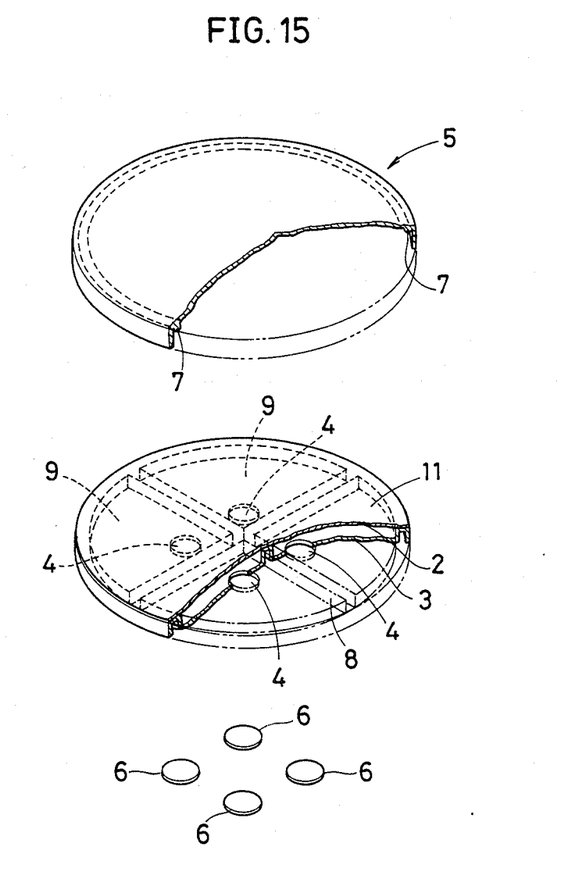
FIG. 15 is a partially cut-away exploded perspective view of the seventh embodiment of the present invention.

FIG. 11 illustrates a case wherein the partitions 8 divide the Petri dish 1 into four sections. According to this embodiment, each section 9 is provided with a small aperture 4. In this case, after the media is poured into each section 9, the small apertures 4 can be sealed with sealing lids 6, respectively. Thus, fear of the bacteria being contaminated is advantagesouly minimized.

FIGS. 12 to 15 illustrate an embodiment using both a pervious sheet 2 and an impervious sheet 11. The mouth of the Petri dish 1 is covered with the pervious sheet 2, which is in turn detachably covered with the impervious sheet 11.

The Petri dish for cultivating bacteria according to the present invention can be utilized for all kinds of agar media except for liquid of semi-fluid media.

Next, a description of an embodiment describing the method of inspecting drug susceptibility of bacteria according to the present invention will be given.

In this embodiment the Petri dish shown in FIGS. 4 to 6, i.e. four-section Petri dish wherein the mouth of the Petri dish 1 is covered with a pervious sheet 2, is used. The Petri dish 1 is provided with partitions 8 whose height is equal to the distance between the bottom 3 of the Petri dish and the pervious sheet 2. The bottom 3 of the Petri dish is provided with small apertures 4 which communicate with all the sections 9 produced by the above-mentioned partitions 8, and the small apertures 4 are sealed with a sealing lid 6.

Porous poly vinylidene fluoride membrane (bore: 0.45 microns) is used as the above-mentioned pervious sheet 2. Using Muller-Hinton agar medium as the medium, a fixed amount of diluted solution of each drug is added to the medium in order to obtain the drug concentrations shown in Table 1. One section of the Petri dish is left as a control and the media are poured separately three steps by three steps into three sections 9 and solidified therein in accordance with the drug concentration. (Since the operation requires three steps per Petri dish, twelve steps in total are required for the operation and four Petri dishes are needed). As the control medium, Muller-Hilton medium is separately poured.

First of all, pus from a patient, as a specimen, is manually inoculated on the pervious sheet 2 of the above-mentioned four-fraction Petri dish.

Next, the pus is inoculated by direct method, using a spiral plater (made by Spiral System instruments, U.S.A.). This spiral plater, which is an inoculating device incorporated into an automatic system for measuring the number of live bacteria, developed and evaluated by the FDA in the U.S.A., performs the inoculation process such that the material to be tested is spirally smeared on the medium, while the material to be tested is being given any of its density gradient which is subject to the distance from the center of the medium.

For this reason, according to the method of the present invention, if the material to be tested is smeared on the pervious sheet 2 for inoculation at the predetermined density gradient, measuring the isolated colonies per fixed area is simple to complete and enables the total number of live bacteria contained in the unit quanity of material to be tested and counted out. Furthermore, of course, in addition to drug susceptibility value in accordance with conventional standards, patterns of the sensitivity of the bacteria causing a particular disease in relation to each drug at its various concentrations stages can be easily and rapidly obtained.

When using the above-mentioned spiral plater, the pathogenic bacteria in this specimen, staphylococcus aureus, is isolated at the rate of $2.8 \times 10^4$ CFU/ml.

Using conventional judgment standards based on the existance of growth, from Table 1 a judgment can be made that the MIC value of ABPC to the above-mentioned isolated bacteria is 1.5 μg/ml, that the MIC value of CTM with respect thereto is 0.78 μg/ml, and the; MIC of CZX, CM, and NFLX with respect thereto are 6.25, over 50, 3.13 μg/ml, respectively.

Paying attention to changes in the number of isolated colonies at the corresponding concentration of each drug may suggest that according to conventional standards, the MIC value of GM is over 50 μg/ml, but actually, at a concentration of 6.25 μg/ml about 50% of the bacteria tested shows sensitivity.

tion, filling the Petri dish with medium does not require that the Petri dish lid 5 be opened so that the media may be separately poured therein and makes it possible for the Petri dish to be turned reversably while the Petri dish lid 5 is being fitted. Also, the media are separately poured into the Petri dish from the small opening 4 provided on the bottom of the Petri dish. For this reason, since the Petri dish lid 5 need not be opened when separately pouring media into the dish, there is less chance of contamination by various bacteria in comparison with conventional types of Petri dishes.

Also, when the pervious sheet 2 is used, the medium is solidified on the pervious sheet 2 working as a bottom surface, and the pervious sheet 2 acts as the cultivation surface, when the media are provided for both inoculation and cultivation. Thus, solidification of the medium need not be performed on a flat table as required conventionally, and vibrations during solidification do not cause turbulence on the surface of the medium. When using the impervious sheet 11, if the impervious sheet 11 is uncovered when the medium is provided for inoculation and cultivation, the same effect can also be obtained.

When using the sectioned (or fractionalized) Petri dish in accordance with the present inventin, the height of the cultivation surface of the media with which each fraction is filled is unified by the pervious sheet 2 or the impervious sheet 11. Therefore, inoculation by an automatic inoculating device such as a spiral plater, which has problems when used with conventional fractionalized Petri dishes due to differences in the levels of the media between the partitions 8, becomes possible. Also, when performing manual inoculation, it is possible inoculate bacteria in a majority of media with one operation.

Furthermore, when using the Petri dish with the pervious sheet 2, the shape of the medium with which the Petri dish 1 is filled is restricted by the Petri dish 1 and the pervious sheet 2. Therefore, when resin of higher water absorbency, including polyacrylic soda, starch polyacrylate, PVA, etc., or a solidifying agent including alginic acid orginating from natural substances and carboxy methyl cellulose, is sealed in the Petri dish 1, filling with a liquid medium is also possible. Thus, preparation of a medium containing a drug which conventionally requires a very complicated procedure

TABLE 1

Pathogenic bacteria: *Staphylococcus aureus*
Controlling medium: Müller-Hinton medium ($2.8 \times 10^4$ CFU/ml)

| Drug concentration (μg/ml) | ABPC (CFU/ml) | CTM (CFU/ml) | CZX (CFU/ml) | GM (CFU/ml) | NFLX (CFU/ml) |
|---|---|---|---|---|---|
| 0.025 | $2.7 \times 10^4$ | $2.9 \times 10^4$ | $2.8 \times 10^4$ | $2.9 \times 10^4$ | $2.8 \times 10^4$ |
| 0.05 | $2.8 \times 10^4$ | $2.6 \times 10^4$ | $2.9 \times 10^4$ | $2.6 \times 10^4$ | $2.8 \times 10^4$ |
| 0.1 | $2.9 \times 10^4$ | $2.9 \times 10^4$ | $2.7 \times 10^4$ | $2.9 \times 10^4$ | $2.6 \times 10^4$ |
| 0.2 | $2.6 \times 10^4$ | $2.6 \times 10^4$ | $3.0 \times 10^4$ | $2.6 \times 10^4$ | $2.9 \times 10^4$ |
| 0.39 | $4.3 \times 10^3$ | $1.8 \times 10^4$ | $2.7 \times 10^4$ | $2.6 \times 10^4$ | $2.8 \times 10^4$ |
| 0.78 | $1.2 \times 10^2$ | 0 | $2.5 \times 10^4$ | $2.9 \times 10^4$ | $2.7 \times 10^4$ |
| 1.56 | 0 | 0 | $5.8 \times 10^3$ | $2.9 \times 10^4$ | $3.5 \times 10^3$ |
| 3.13 | 0 | 0 | $3.6 \times 10^2$ | $2.6 \times 10^4$ | 0 |
| 6.25 | 0 | 0 | 0 | $1.7 \times 10^4$ | 0 |
| 12.5 | 0 | 0 | 0 | $8.0 \times 10^3$ | 0 |
| 25 | 0 | 0 | 0 | $6.8 \times 10^3$ | 0 |
| 50 | 0 | 0 | 0 | $6.2 \times 10^3$ | 0 |

ABPC: ampicillin
CTM: cefotiam
CZX: ceftizoxime
GM: gentamicin
NFLX: norfloxacin According to the present invention, since the Petri dish for cultivating bacteria has the foregoing construcis easily performed in the present invention. In addition, if each of the sections 9 of the Petri dish 1 is filled with media which contain different concentrations of a particular drug, the Petri dish of the present invention can further be used conveniently for drug susceptibility testing.

When the Petri dish with the impervious sheet 11 is used, during storage and transit after the Petri dish is filled with media, the media is sealed between the impervious sheet 11 and the Petri dish 1. Thus, the media does not contact air and drying out and/or deterioration due to oxidation is prevented. Also, the cultivation surface of the media is prevented from getting wet due to humidity and further prevented from getting contaminated by various types of bacteria during storage. Since it is possible for media poured separately in the Petri dish to be stored in a state screened from air, when cultivating anaerobic bacteria, if media deareated in advance by pressure reduction, boiling, ultrasonic treatment, etc. are separately poured, a medium can be provided which has a small amount of dissolved oxygen in it than conventional media.

Incidentally, the Petri dish for cultivating bacteria according to the present invention can also be used to screen pathogenic bacteria with several pieces of dishes by varying adequate media in their respective sections.

According to the method of the present invention, since utilization of the pervious sheet 2 as the cultivation surface enables an extremely flat cultivation surface to be obtained in spite of the use of a fractionalized Petri dish, in addition to making manual bacteria inoculation easier, it is possible to utilize an automatic inoculating device such as a spiral plater.

We claim:

1. A round Petri dish for cultivating bacteria characterized in that an upper edge of a circular mouth of said Petri dish is detachably covered with at least one sheet which is impervious to the component of the media with which the inside of said Petri dish is filled and is impervious to water and oxygen, at least one small circular aperture is provided in a bottom of said Petri dish and a top surface of the small aperture lies in a plane passing through the upper edge of the Petri dish.

2. A Petri dish as defined in claim 1, wherein said small aperture is detachably provided with a sealing lid.

3. A Petri dish according to claim 1, wherein said Petri dish is made from plastic.

4. A Petri dish according to claim 3, wherein said impervious sheet is a synthetic resin membrane or film which is high in oxygen gas barrier properties and is selected from the group consisting of polyacrylonitrile nylon, polymethacrylonitrile, ethylene vinyl alcohol polymer, polyvinylidene chloride, polyethylene terephthalate and polyvinyl chloride.

* * * * *